United States Patent
Furlong et al.

(10) Patent No.: US 6,927,296 B2
(45) Date of Patent: Aug. 9, 2005

(54) PROCESS

(75) Inventors: Patrick Joseph Furlong, Cork (IE); Cornelius Joseph Kelly, Cork (IE); Ronald James Ogilvie, Sandwich (GB); Vincent Ryan, Cork (IE)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/894,446

(22) Filed: Jul. 19, 2004

(65) Prior Publication Data

US 2005/0020663 A1 Jan. 27, 2005

Related U.S. Application Data

(60) Provisional application No. 60/511,182, filed on Oct. 14, 2003.

(30) Foreign Application Priority Data

Jul. 23, 2003 (GB) .............................. 0317229

(51) Int. Cl.[7] .............................................. C07D 403/06
(52) U.S. Cl. ........................................................ 548/465
(58) Field of Search .......................................... 548/465

(56) References Cited

U.S. PATENT DOCUMENTS 5,607,951 A        3/1997  Macor et al.
2003/0166704 A1 *  9/2003  Ogilvie ....................... 514/414

FOREIGN PATENT DOCUMENTS

| EP | 1088817 A2      | 9/2000 |
| WO | WO 96/06842 A1  | 3/1996 |
| WO | WO 00/32589 A1  | 6/2000 |
| WO | WO 02/50063 A1  | 6/2002 |

* cited by examiner

Primary Examiner—Patricia L. Morris
(74) Attorney, Agent, or Firm—Charles W Ashbrook; David R Kurlandsky

(57) ABSTRACT

The present invention provides an improved process for the preparation of α-polymorphic eletriptan hydrobromide.

4 Claims, No Drawings

PROCESS

This application is a United States utility application, which claims the benefit of priority to United Kingdom application Serial No. 0317229.3 filed Jul. 23, 2003 and U.S. provisional application Ser. No. 60/511,182 filed Oct. 14, 2003.

The present invention relates to an improved process for the preparation of the α-polymorphic crystalline form of eletriptan hydrobromide.

Eletriptan, 3-{[1-methylpyrrolidin-2(R)-yl]methyl}-5-(2-phenylsulfonylethyl)-1H-indole, and a process for its preparation, are disclosed in U.S. Pat. No. 5,607,951. Further processes for the preparation of eletriptan are disclosed in EP-B-1088817 and WO-A-02/50063.

Eletriptan hydrobromide has the structure of formula (I) below.

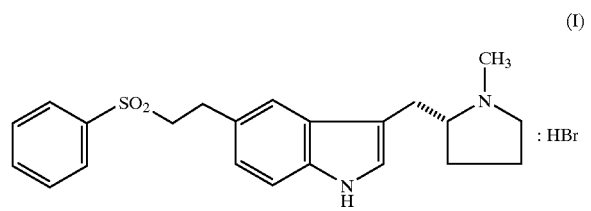

(I)

WO-A-96/06842 discloses eletriptan hydrobromide, two of its crystalline forms and processes for the preparation thereof. One of the crystalline forms disclosed therein, designated the α-form, is currently marketed as a treatment for migraine under the name Relpax™.

WO-A-00/32589 discloses a crystalline monohydrate of eletriptan hydrobromide and processes for its preparation.

Two processes for the conversion of eletriptan free base to the α-polymorph of eletriptan hydrobromide are disclosed in WO-A-96/06842. According to the first process, a solution of eletriptan in acetone is treated with an aqueous solution of hydrogen bromide and the resulting oil is crystallised from 2-propanol. According to the second process, a solution of eletriptan in acetone is treated with an aqueous solution of hydrogen bromide and the reaction mixture is slurried, heated at reflux, cooled and slurried a second time.

Under large scale conditions, the yield of eletriptan hydrobromide using these prior art processes is in the region of 73%.

It will be appreciated that in the preparation of sufficient quantities of eletriptan hydrobromide to satisfy the global market for Relpax™, increases in yield, particularly in a late-stage step of the commercial process, are extremely significant in reducing the cost of drug product and are consequently of high commercial importance. Any successful process must also be robust in the sense of reliably producing a homogeneous product containing the same crystalline form, free of other crystalline forms and solvates.

It has now been surprisingly found that a high yielding and robust process for the preparation of the α-polymorph of eletriptan hydrobromide is provided by (a) treating a solution of eletriptan in 2-butanone with hydrobromic acid and (b) distilling off a 2-butanone/water azeotrope until formation of anhydrous α-polymorphic eletriptan hydrobromide is complete.

The yield obtained when using this process on a large scale is in the region of 93 to 96%. The product obtained is exclusively the α-polymorph of eletriptan hydrobromide; no other polymorphic forms or solvates have been observed. Advantageously, the product obtained has a desirable white colouration.

The product of step (a) is thought to be a hydrate, probably the monohydrate described in WO-A-00/32589. This hydrate is then converted in step (b) to form the desired product.

The eletriptan starting material is preferably dry (less than 0.3% water by Karl Fisher analysis) and free of particulate impurities (the solution in 2-butanone can be filtered if necessary). The hydrobromic acid is preferably a 48% aqueous solution and is advantageously added to the reaction vessel as a solution in 2-butanone, over a period of at least an hour and at room temperature. This form of addition ensures that the pH of the reaction mixture does not fall below 5 and leads to a cleaner reaction and a higher yield. The use of from 0.95 to 1.05 molar equivalents of hydrobromic acid is preferred, the use of 0.98 molar equivalents being optimal. About 21 litres of 2-butanone per kilogram of eletriptan starting material should preferably be used in total. After addition of the hydrobromic acid, the reaction is stirred, preferably for a period of at least 3 hours.

During the azeotropic distillation, substantially all the water should be removed from the reaction mixture. A final water content of less than 0.5% weight/weight is preferred. Where about 21 litres of 2-butanone per kilogram of eletriptan starting material has been used in conjunction with 0.98 equivalents of 48% hydrobromic acid, a final volume of about 11 litres per kilogram of eletriptan is ideal.

The product is conveniently isolated by filtration. Typically, the reaction mixture is allowed to cool slowly to room temperature, optionally granulated, filtered, washed with further 2-butanone and dried.

The α-polymorphic eletriptan hydrobromide prepared by the above process may optionally be subjected to a further processing step, known as a polymorph annealing step, which increases its resistance to subsequent hydration. Thus, according to optional step (c), the product of step (b) is slurried in refluxing toluene and a proportion of the toluene is removed by distillation. Preferably, at least 12% of the toluene is removed; most preferably about 16.5% is removed. Step (c) may be optionally repeated.

An initial volume of 15 litres of toluene per kilogram of eletriptan hydrobomide is preferred. For optimal results, the distillation of toluene should be repeated twice and the reaction mixture should be heated at a sub-reflux temperature for a minimum of two hours in between the distillations. A sub-reflux temperature of about 106° C. is ideal. The final product is conveniently isolated by filtration. Typically, the reaction mixture is cooled to room temperature, granulated, filtered, washed with further toluene and dried.

Step (c) is advantageously carried out under an atmosphere of nitrogen to prevent discolouration of the product.

A further embodiment of the invention provides a process for generating stable α-polymorphic eletriptan hydrobromide from any other polymorphic and/or solvated/hydrated form of eletriptan hydrobromide or from a mixture of different polymorphic and/or solvated/hydrated forms (including a mixture comprising the α-polymeric form itself).

This conversion process comprises the steps of (a) crystallising a solution of the eletriptan hydrobromide starting material in a mixture of 2-butanone and water and (b) distilling off a 2-butanone/water azeotrope until formation of anhydrous α-polymorphic eletriptan hydrobromide is complete. An optional annealing step (c), as described above, may also be carried out.

This process is particularly advantageous since previously the only viable large scale process for converting mixed polymorphic and/or solvated/hydrated forms of eletriptan hydrobromide to the pure α-polymorph of eletriptan hydrobromide involved breaking the salt to the free base as a preliminary step.

Eletriptan is preferably prepared according to Scheme 1 below.

Conveniently, compound (II) may be converted to compound (IV) without isolation of compound (III).

Compound (V) ((R)-5-(2-phenylsulphonylethenyl)-3-(N-methylpyrrolidin-2-ylmethyl)-1H-indole) may be prepared by treating a solution of compound (IV) in methanol

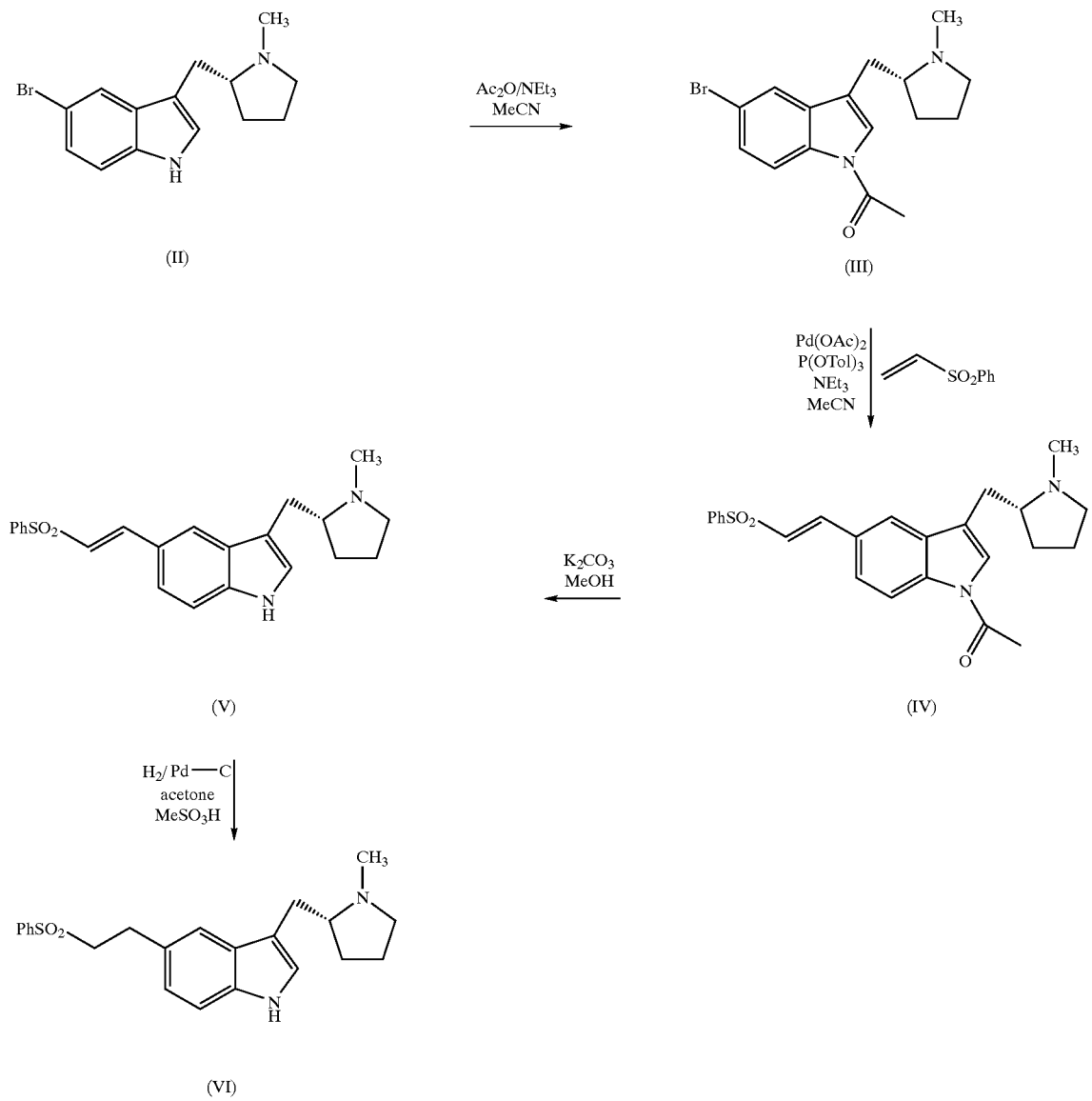

Compound (II) ((R)-5-bromo-3-(N-methylpyrrolidine-2-ylmethyl)-1H-indole) may be prepared by the methods described in U.S. Pat. No. 5,607,951 or EP-B-1088817.

Compound (III) ((R)-1-acetyl-5-bromo-3-(N-methylpyrrolidine-2-ylmethyl)-1H-indole) may be prepared by treating a solution of compound (II) in acetonitrile, with acetic anhydride and triethylamine. The reaction is preferably carried out under reflux.

Compound (IV) ((R)-1-acetyl-5-(2-phenylsulphonylethenyl)-3-(N-methylpyrrolidin-2-ylmethyl)-1H-indole) may be prepared by treating a solution of compound (III) in acetonitrile with triethylamine, tri-o-tolylphosphine, palladium acetate and phenylvinylsulphone. The reaction is preferably carried out under reflux.

with potassium carbonate. The reaction is preferably carried out at room temperature. A similar process, described in the prior art (see Example 58 of U.S. Pat. No. 5,607,951) uses recrystallisation to purify and isolate compound (V). Recrystallisation is indeed an effective means of purification, particularly from a mixture of acetonitrile and water or a mixture of acetone and water, but the yield of product obtained is sub-optimal. Surprisingly, it has been found that column chromatography is a more efficient method of purifying crude compound (V), even on a large multikilogram scale, and a significantly higher yield of product can be isolated in this way.

When chromatography is used to purify compound (V), the methanolic solution resulting from the reaction is filtered and neutralised with an aqueous acid, preferably phosphoric acid. The mixture is then loaded onto a column packed with a suitable stationary phase (preferably a styrene polymer such as CG-161 resin, available from Tosoh Bioscience). The column is eluted with a mixture of acetone and an aqueous acid (preferably acetic or phosphoric acid) and the fractions containing product are combined and concentrated. Acetone is added to the concentrated solution and the pH is adjusted to from 10 to 11 using a suitable base, such as potassium carbonate, to precipitate the product. The product is collected, washed with water and dried.

Compound (VI) (eletriptan) may be prepared by treating a solution of compound (V) in a mixture of acetone and water with palladium on carbon and methanesulphonic acid under an atmosphere of hydrogen. A catalyst comprising 5% palladium on carbon is preferred. A particularly advantageous catalyst for use in this process is PMC 2020C (supplied by the Precious Metals Corporation), requiring a catalyst loading as low as 7%.

The following Examples illustrate particular ways of putting the invention into effect. Differential scanning calorimetry (DSC) was performed using a Perkin Elmer DSC-7 instrument. Approximately 10 mg of each sample was accurately weighed into a 50 microlitre aluminium pan. The samples were heated at 20° C./minute over the range 40° C. to 220° C. with a nitrogen gas purge.

EXAMPLE 1

(a) (R)-5-Bromo-3-(N-methylpyrrolidine-2-ylmethyl)-1H-indole (256 kg), acetonitrile (380 kg), triethylamine (115 kg) and acetic anhydride (115 kg) were charged to a dry glass lined vessel. The reaction mixture was heated to reflux and maintain at this temperature for 4.5 hours.

(b) A mixture of acetonitrile (375 kg), palladium acetate (12.5 kg) and tri-o-tolylphosphine (60 kg) was stirred for 1 hour. Phenyl vinyl sulphone (160 kg), triethylamine (92 kg) and finally the solution prepared in part (a) were added and the mixture was heated to reflux for 7.5 hours. The reaction mixture was cooled and a solution of 190 kg concentrated hydrochloric acid in 1200 kg water was added over 4 hours. The resulting mixture was filtered to remove spent catalyst and a further 3000 kg of water and 300 kg of 50% w/w aqueous sodium hydroxide solution were added to the filtrate to precipitate the product. The resulting suspension was filtered and washed with water (500 kg) to yield crude (R)-1-acetyl-5-(2-phenylsulphonylethenyl)-3-(N-methylpyrrolidin-2-ylmethyl)-1H-indole) as a dark brown, wet, crystalline solid (535 kg wet, equivalent of 338 kg dry). This crude product was added to 530 kg of acetone and the mixture was heated to 60° C. On reaching this temperature 814 kg of water was added over 2 hours whilst simultaneously cooling the mixture back to ambient temperature. The batch was then granulated for 2 hours and filtered to yield the purified product (350 kg wet, equivalent of 280 kg dry, 83%).

EXAMPLE 2

Methanol (660 kg) and (R)-1-acetyl-5-(2-phenylsulphonylethenyl)-3-(N-methylpyrrolidin-2-ylmethyl)-1H-indole (77 kg dry equivalent of the recrystallised product of Example 1) were charged to a vessel and the resulting mixture was stirred for 5 minutes. Potassium carbonate (8.9 kg) was added and the mixture was stirred at room temperature for 30 minutes. The reaction mixture was then warmed to 35° C. and Norit carbon (11.6 kg) and water (235 kg) were added. The resulting mixture was filtered and the filtrate was diluted by the addition of water (1300 kg, added over two hours) and granulated for 2 hours at room temperature. Filtration gave crude (R)-5-(2-phenylsulphonylethenyl)-3-(N-methylpyrrolidin-2-ylmethyl)-1H-indole (75 kg wet, equivalent of 60.5 kg dry, 88%).

EXAMPLE 3

A mixture of acetonitrile (940 kg) and crude (R)-5-(2-phenylsulphonylethenyl)-3-(N-methylpyrrolidin-2-ylmethyl)-1H-indole (478 kg dry equivalent, product of the process of Example 2) was warmed to 55° C. Water (720 kg) was added and the mixture was cooled to 20° C. and granulated for 2 hours at that temperature. Pure (R)-5-(2-phenylsulphonylethenyl)-3-(N-methylpyrrolidin-2-ylmethyl)-1H-indole (482 kg wet, equivalent of 393 kg dry, 82%) was recovered by filtration.

EXAMPLE 4

Acetone (1140 kg) and (R)-5-(2-phenylsulphonylethenyl)-3-(N-methylpyrrolidin-2-ylmethyl)-1H-indole (482 kg dry equivalent, recrystallised product of Example 3) were charged to a vessel and the mixture was warmed to 55° C. Water (1520 kg) was added and the mixture was cooled to 20° C. and granulated for 2 hours. Recrystallised (R)-5-(2-phenylsulphonylethenyl)-3-(N-methylpyrrolidin-2-ylmethyl)-1H-indole (492 kg wet, 343 kg dry equivalent, 87%) was isolated by filtration.

EXAMPLE 5

(R)-5-(2-Phenylsulphonylethenyl)-3-(N-methylpyrrolidin-2-ylmethyl)-1H-indole (200 kg dry equivalent) and acetone (1186.5 kg) were charged to a dry, glass lined vessel. De-ionised water (300 kg), further acetone (237 kg), methanesulphonic acid (55 kg) and a slurry of palladium on carbon (22.4 kg dry equivalent) in de-ionised water (200 kg) were added and the mixture was hydrogenated under an atmosphere of hydrogen gas. The reaction slurry was filtered to remove the catalyst. De-ionised water (1300 kg) and 48% aqueous sodium hydroxide solution (60 kg) were added to precipitate the product, which was isolated by filtration and washed with a mix of de-ionised water (210 kg), acetone (83 kg) and further de-ionised water (710 kg) to yield 3-{[1-methylpyrrolidin-2(R)-yl]methyl}-5-(2-phenylsulphonylethyl)-1H-indole (220 kg wet, 157.65 kg when dry, 78.41%).

EXAMPLE 6

3-{[1-Methylpyrrolidin-2(R)-yl]methyl}-5-(2-phenylsulphonylethyl)-1H-indole (15 kg) and 2-butanone (204 kg) were charged to a dry, glass-lined vessel. A solution of 48% aqueous hydrobromic acid (6.45 kg) in 2-butanone (63 kg) was added and the resulting slurry was subjected to azeotropic distillation until a volume of 150 litres remained. The reaction mixture was cooled to 17.5° C. and the product was isolated by filtration. The product was washed with 2-butanone (16 kg) to yield the α-polymorphic form of 3-{[1-Methylpyrrolidin-2(R)-yl]methyl}-5-(2-phenylsulphonylethyl)-1H-indole hydrobromide (18.2 kg wet, 17.5 kg when dry, 96.3%).

DSC: A single major endotherm with a peak maximum in the range 173°–179° C. was observed, indicative of the α-polymorph (see WO-A-96/06842).

EXAMPLE 7

α-Polymorphic 3-{[1-methylpyrrolidin-2(R)-yl]methyl}-5-(2-phenylsulphonylethyl)-1H-indole hydrobromide (300 kg) and toluene (3892 kg) were charged to a dry, glass-lined vessel. The resulting slurry was heated under reflux and approximately 666 kg of toluene was removed by distillation. The slurry was cooled to 100–105° C. and then a further 666 kg of toluene was removed by distillation. The reaction slurry was then cooled to 22.5° C. and the product was isolated by filtration. The product was washed with toluene (908 kg) to yield α-polymorphic 3-{[1-methylpyrrolidin-2(R)-yl]methyl}-5-(2-phenylsulphonylethyl)-1H-indole hydrobromide (289 kg dry weight, 96.3%).

DSC: A single major endotherm with a peak maximum in the range 173°–179° C. was observed, indicative of the α-polymorph (see WO-A-96/06842).

EXAMPLE 8

3-{[1-Methylpyrrolidin-2(R)-yl]methyl}-5-(2-phenylsulphonylethyl)-1H-indole hydrobromide (10 kg), 2-butanone (63 kg) and de-ionised water (0.65 kg) were charged to a dry, glass-lined vessel and heated to 67.5° C. to form a solution. The solution was then cooled to 60° C. and further 2-butanone (42 kg) was added to precipitate the product. The resulting slurry was subjected to an azeotropic distillation to leave a final reaction volume of 50 litres and then cooled to 22.5° C. The product was isolated by filtration and washed with 2-butanone (10.5 kg) to yield α-polymorphic 3-{[1-methylpyrrolidin-2(R)-yl]methyl}-5-(2-phenylsulphonylethyl)-1H-indole hydrobromide (9.3 kg dry weight, 93%).

DSC: A single major endotherm with a peak maximum in the range 173°–179° C. was observed, indicative of the α-polymorph (see WO-A-96/06842).

Comparative Example

3-{[1-Methylpyrrolidin-2(R)-yl]methyl}-5-(2-phenylsulphonylethyl)-1H-indole (274 kg) and acetone (3419 kg) were charged to a dry, glass-lined vessel. A solution of 48% aqueous hydrobromic acid (114.7 kg) in acetone (1383 kg) was added at a temperature of from 50 to 55° C. over 1 hour and the resulting slurry was stirred for 4 hours. The reaction mixture was cooled to from 30 to 35° C. and the product was isolated by filtration. The product was washed with acetone (861 kg) to yield the α-polymorphic form of 3-{[1-methylpyrrolidin-2(R)-yl]methyl}-5-(2-phenylsulphonylethyl)-1H-indole hydrobromide (242.4 kg dry, 73.0%).

DSC: A single major endotherm with a peak maximum in the range 173°–179° C. was observed, indicative of the α-polymorph see WO-A-96/06842).

What is claimed is:

1. A process for preparing α-polymorphic eletriptan hydrobromide comprising the steps of (a) treating a solution of eletriptan in 2-butanone with hydrobromic acid and (b) distilling off a 2-butanone/water azeotrope until formation of anhydrous α-polymorphic eletriptan hydrobromide is complete.

2. A process as claimed in claim 1 wherein the water content of the reaction mixture is reduced to less than 0.5% weight/weight in step (b).

3. A process as claimed in claim 1 comprising the extra step of slurrying the product of step (b) in refluxing toluene and removing a proportion of the toluene by distillation.

4. A process as claimed in claim 3 wherein at least 12% of the toluene is removed.

\* \* \* \* \*